United States Patent [19]

Tramier

[11] 3,933,855

[45] Jan. 20, 1976

[54] PRODUCTION OF ORGANIC SULPHOXIDES
[75] Inventor: Bernard Tramier, Pau, France
[73] Assignee: Societe Nationale des Petroles d'Aquitaine, Paris, France
[22] Filed: June 29, 1973
[21] Appl. No.: 375,163

[30] Foreign Application Priority Data
June 30, 1972 France .............................. 72.23668

[52] U.S. Cl....... 260/329 R; 260/607 A; 260/607 D
[51] Int. Cl.² ........................................ C07D 333/48
[58] Field of Search ......... 260/329 R, 607 A, 607 D

[56] References Cited
UNITED STATES PATENTS
3,428,671   2/1969   Toland .............................. 260/51.3

*Primary Examiner*—Henry R. Jiles
*Assistant Examiner*—C. M. S. Jaisle
*Attorney, Agent, or Firm*—Ostrolenk, Faber, Gerb & Soffen

[57] ABSTRACT

Production of organic sulphoxides by the action of sulphoxides of lower molecular weight on organic sulphides in which the reaction is catalysed by one or more substances capable of supplying hydrogen ions to the reaction medium. The process permits yields to be obtained which exceed 90 percent, and the sulphoxide which is obtained is practically free from sulphone.

9 Claims, No Drawings

PRODUCTION OF ORGANIC SULPHOXIDES

The present invention relates to the production of organic sulphoxides. It is concerned with a process for obtaining these compounds by the action of sulphoxides of lower molecular weight on organic sulphides.

Now that dimethyl sulphoxide has acquired a very important place in industry, particularly as a solvent for an extremely wide range of uses, other sulphoxides, especially its homologues, have also proved to be of interest, for example, in the fields concerned with surface-active agents, detergents, cosmetics, pesticides, in the textile industries, as uranium extraction solvents, etc. For some years, attempts have also been made to manufacture different organic sulphoxides, and especially dialkyl sulphoxides in which the alkyls have more than 1 carbon atom. The oxidation of the corresponding sulphides by conventional oxidising agents, as for example hydrogen peroxide, nitric acid, nitrogen dioxide, etc., generally leads to the formation of sulphone; on the other hand, the nitrogen oxides present the danger of explosion, which limits their use solely to the manufacture of lower alkyl sulphoxides. Some progress has been achieved by using dimethyl sulphoxide as a gentle oxidant: in a scientific paper dated 1958, SEARLES and HAYS (Journ. Org. Chem. vol. 23–1958 page 2,028) indicate yields of 55 to 59 percent of di-n.propyl, di-n.butyl and tetramethylene sulphoxides, obtained by the action of $CH_3SOCH_3$ on the corresponding sulphides. However, these authors say that they have not been able to obtain by this method sulphoxide from sulphides such as that of diisopropyl. Furthermore, they attempted catalysing the reaction with acids, but were not successful.

The action of lower alkyl sulphoxides on organic sulphides was later investigated by researchers, who found that the bromide ion catalyses the reaction; this work is described in US Pat. No. 3,428,671 of 1969, according to which any soluble salt with a BR ion, HBr or even elementary bromine are suitable as catalyst. Using ammonium bromide, the authors obtain from di-n.butyl sulphide and dimethyl sulphoxide, di-n.butyl sulphoxide with a yield not exceeding 34.4 percent (27.9 g of crude product, starting with 73 g of sulphide), that is to say, even less than SEARLES and HAYS.

The problem of economically obtaining a sulphoxide of high molecular weight by the action of a sulphoxide of lower molecular weight on the corresponding organic sulphide thus still remains. The present invention provides a solution thereof: it permits the preparation of all kinds of sulphoxides, by the aforementioned reaction, with suitable yields which are acceptable industrially, particularly yields of 60 to 95 percent based on the starting sulphide. In addition, it leads to very good selectivities as regards the sulphoxide being sought, especially of about 75 to 100 percent. The process according to the invention makes it possible to obtain these results in a shorter time, generally of the order of 30 minutes to 5 hours.

The invention results from the unexpected discovery that, contrary to the aforementioned publications, the reaction concerned is catalysed by the $H^+$ ions.

The new process according to the invention consists in heating an organic sulphide with an excess of dialkyl sulphoxide, of which the alkyls have a number of carbon atoms lower than that of the organic radicals of the sulphide, the mixture containing at least one substance capable of yielding $H^+$ ions in the reaction medium.

Interesting results are particularly obtained with mono-acids or acid salts, of which the molecule is capable of supplying a single hydrogen ion. In addition, the reaction medium must contain a small quantity of water, when the acid or salt being used is not sufficiently ionised in dry dialkyl sulphoxide.

It is evident that the acids or salts used as catalyst according to the invention must be selected from those which do not cause any secondary reactions, for example, oxidation or reduction of the reagents which are present.

Since strong electrolytes are preferred, the catalysts can with advantage be mineral acids or weak base salts of such acids. Especially suitable are the perchloric, hydrochloric, hydrofluoric, hydrobromic, hydriodic, nitric acids, etc. and their salts with ammonium, for example perchlorates, chlorides and bromides, etc.

The preferred manner of using these catalysts consists in introducing them, into the reaction medium, in the form of an aqueous solution; the concentration of this solution can vary widely, for example, between 0.1 and 10M and preferably between 2 and 6M, the best concentration moreover depending on the nature of the catalyst.

According to one particular feature of the invention, the quantity of catalyst is adjusted so that the reaction medium contains 0.5 to 3 gram-ions of hydrogen available per 100 moles of sulphide being used. The best proportion is about 1 to 2 hydrogen gram-ions per 100 moles of sulphide. It has in fact been established that the speed of reaction depends on the quantity of catalyst.

According to a preferred feature of the invention, a current of inert gas is blown through the reaction medium; the inert gas, particularly nitrogen, permits the formed sulphide to be carried away in proportion to its formation; the elimination achieved in this way of the sulphide favours the displacement of the equilibrium reaction towards the formation of the required sulphoxide.

On the other hand, the heating time of the reaction medium plays an important part: according to the invention, the preferred form of procedure consists in stopping the reaction as soon as the maximum yield possible in the given case has been reached. If the heating is continued, the conversion of the sulphide can still increase, but the selectivity as regards sulphoxide is lowered and with it the yield.

Thus, according to one particular feature of the invention, the maximum yield as a function of time is determined in advance in each particular case; then, during industrial production, the reaction is stopped after the time which was found to be that corresponding to the best yield. Depending on the nature of the acid catalyst which is used and depending on the concentration of said catalyst, the operation usually lasts from one to twelve hours, at a temperature close to but below the boiling point of the sulphoxide which is employed. This time also depends on the nature of the sulphide which is used. Thus, with 1 to 3 ml of a 2M to 10M solution of mono-acid or of acid salt in water, for 100 ml of sulphixode of lower molecular weight, at about 170°C, the reaction is generally achieved in 2 to 6 hours.

Although the symmetrical or asymmetrical and possibly hydroxylated dialkyl sulphides are particularly suitable for carrying out the invention, it is however also possible to use dicycloalkyl or diaryl sulphides, or even mixed sulphides of alkyls and/or cycloalkyls or aryls. In the case of alkyls, it is particularly preferred to use those of which the number of carbon atoms is from 2 to 18. On the other hand, the sulphide may in itself be cyclic, as is the case with tetramethylene sulphide (tetrahydrothiophene).

The invention is illustrated by the following non-limiting examples. In these examples, 0.5 mole of organic sulphide, 0.75 mole of dimethyl sulphoxide (58.6 g) and 1.5 ml of an aqueous solution of the selected catalyst were introduced into a spherical flask. A stream of nitrogen was sent through the formed mixture and the latter was then brought to 170°C. The flask, equipped with a condenser regulated to 50°–60°C, permitted the initial sulphide and the dimethyl sulphoxide to condense, but not the formed dimethyl sulphide; this latter can thus be eliminated. The reaction temperature is maintained for a predetermined time, while the vapours of dimethyl sulphide are eliminated and recovered. The dimethyl sulphoxide, entrained by the sulphide, is separated by decantation and recycled. When the reaction is terminated, the reaction mixture is cooled and the formed sulphoxide is separated therefrom, either by distillation or by filtration, when this sulphoxide crystallises. The first runnings from the distillation, or even the filtrate, can be recovered and recycled. This represents a decided advantage as compared by the process using hydrogen peroxide, which leads to sulphoxide in water, the separation of which is difficult for hydrosoluble sulphoxides.

In the tables which recapitulate examples, the nature of the catalysts and the concentration of their aqueous solutions as regards molarity (M) are indicated. The yields are related to the sulphide which is used. It can be seen that the molar excess of dimethyl sulphoxide is 50 percent, based on the starting sulphide; in accordance with the prior art, it is important to have an excess of this reagent, but it is sufficient to have a proportion of 1.1 to 2 moles of sulphoxide per 1 mole of initial sulphide, instead of an excess as large as 3 or 4 moles, which is specified in US Pat. No. 3,428,671.

It is shown by Examples 1 to 18 that the aqueous, acid catalysts according to the invention permit yields to be obtained which extend to beyond 90 percent (Example 2). In the case where the yields are of the order of 55 to 60percent, 60 is to say, the same as those which were achieved by SEARLES and HAYS, the operating time is nevertheless much shorter than in the work carried out by these authors; thus, 55 percent are reached in Example 14 in 3 hours and in Example 15 in 1½ hours; a yield of 62 percent is reached in Example 10 in three-fourths of an hour; now, according to the aforesaid article in the Journal of Organic Chemistry, yields of 55 to 59 percent were obtained after 8 to 12 hours.

It is also possible to verify a substantial progress by comparison with the results of US Pat. No. 3,428,671: in fact, in Example 5 of the patent, the use of ammonium bromide led to a yield not exceeding 34.4percent, whereas the aqueous solution of this bromide, in accordance with the present invention, gave yields of at least 55 percent and capable of exceeding 90 percent.

In addition, it is interesting to confirm that aqueous solutions of potassium bromide (Example 16) do not in any way catalyse the reaction, although the cited US Patent indicates the bromide ion generally as catalyst. The comparison between the results of Examples 16 and 17, on the one hand, and 1 to 15, on the other hand, clearly shows that it is the acid substances or compounds capable of liberating an acid which catalyse the reaction.

EXAMPLES 19 to 26

In order to make clear the significance of the concentration of the aqueous solution in acid substance serving as catalyst, a series of preparations of di-n.propyl sulphoxide from dipropyl sulphide and dimethyl sulphoxide was carried out, under the general conditions of Examples 1 to 18. The catalyst used was an aqueous solution of ammonium hydrobromide. The reaction was stopped after time periods which varied.

The following table sets out the results of these tests; it also contains as a comparison the results of Examples 12 and 13.

EXAMPLES 1 to 18

| No. | Sulphide of | Catalyst | | Reaction time (hours) | Yield % |
|---|---|---|---|---|---|
| 1 | dipropyl | HClO₄ | 0.1M | 12 | 89 |
| 1A | diisopropyl | " | " | " | 90 |
| 2 | dibutyl | " | " | " | 92 |
| 3 | diheptyl | " | " | " | 70 |
| 4 | dipropyl | HNO₃ | 0.1M | 16 | 60 |
| 5 | " | HCl | " | 40 | 60 |
| 6 | " | " | 4M | 4 | 68 |
| 7 | " | HBr | 0.1M | 16 | 51 |
| 8 | " | " | 4M | 3.5 | 85 |
| 9 | dibutyl | " | " | " | 87 |
| 10 | methyl and dodecyl | " | " | 0.75 | 62 |
| 11* | (tetrahydrothiophene) | " | " | 2 | 78 |
| 12 | dipropyl | NH₄Br | 1M | 7.5 | 67 |
| 13 | " | " | 10M | 5 | 72 |
| 14 | " | NH₄I | 4M | 3 | 55 |
| 15 | diheptyl | NH₄Br | 10M | 1.5 | 55 |
| 16 | dipropyl | KBr | 4M | 12 | 0 |
| 17 | " | KI | " | 12 | 0 |
| 18 | methyl and heptyl | HCl | 4M | 4 | 68 |

*Tetramethylene sulphide.

EXAMPLES 19 to 26

| Ex. No. | Catalyst NH₄Br | Time (hours) | Conversion % | Selectivity % | Yield % |
|---|---|---|---|---|---|
| 19 | 0.1M | 16.5 | — | — | 50 |
| 12 | 1M | 7.5 | — | — | 67 |
| 20 | 4M | 2 | 90 | 100 | 90 |
| 21 | 10M | 4 | 66 | 100 | 66 |
| 13 | " | 5 | 81 | 89 | 72 |
| 22 | " | 6 | 84 | 82 | 69 |
| 23 | " | 7 | 84 | 70 | 59 |
| 24 | 10M+ HClO₄ 0.1M | 2 | 80 | 100 | 80 |
| 25 | " | 3 | 82 | 97.5 | 80 |
| 26 | " | 5 | 89 | 92 | 81.5 |

It is possible from these results to reach the conclusion that the optimum value as regards concentration of acid catalyst in the aqueous solution added to the reaction medium is at or close to 4M (Example 20); as the quantity of this added solution was 1.5 ml, this represents 1.2 moles of NH₄Br with about 10 moles of H₂O for 100 moles of dipropyl sulphide. It is seen that these proportions permit the selectivity of 100percent to be reached for a yield of 90 percent On the other hand, Examples 21, 13, 22 and 23, all carried out with a 10M solution of hydrobromide, show how the rate of conversion increases, while the selectivity decreases, in time; hence, a selectivity of 100 percent is found after 4 hours (Example 21), while the optimum value of the yield of 72 percent is obtained after 5 hours, the selectivity having fallen to 89 percent. The disclosure of these facts within the scope of the present invention makes possible a judicious choice of the heating time with a view to obtaining the best industrial result.

Another useful piece of information which confirms the duty of the H$^+$ ions is apparent from Examples 24 to 26: here, a small addition of strong acid (perchloric acid) to the same 10M hydrobromide of Examples 21 to 23 and 13, shows a substantial improvement in the selectivities and yields. This addition permits (Example 24) a selectivity of 100 percent to be obtained in 2 hours with a yield of 80percent, instead of taking 4 hours as in Example 21, where the yield was only 66 percent.

Although the examples are concerned with operations carried out at 170°C with dimethyl sulphoxide as oxidant, the invention can likewise be carried out at other sufficiently high temperatures, particularly from 150° to 250°C, with other sulphoxides; in each case, the temperature is equal to or below the boiling point of the reaction mixture. It is expedient to operate with a reflux condenser when working at this boiling point.

In the case of hydroxylated alkyl sulphoxides which, by the known methods give very small yields, the present invention provides a substantial improvement, as shown by Examples 27 and 28.

EXAMPLE 27

Under the general conditions which are described in connection with the foregoing examples, dimethyl sulphoxide is caused to react with β-hydroxyethyl and octyl sulphide

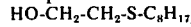
HO-CH$_2$-CH$_2$-S-C$_8$H$_{17}$ in the presence of 4M HBr. After 5 hours, the conversion rate to β-hydroxyethyl and octyl sulphoxide was 25 percent. By contrast, the oxidation with hydrogen peroxide of the same initial sulphide, using the conventional method, only gave a conversion of 15 percent.

EXAMPLE 28

Thiodiglycol, i.e., diglycol sulphide (CH$_2$-CH$_2$-OH)$_2$S is subjected firstly to oxidation with dimethyl sulphoxide, in the same way as Example 27, and secondly to conventional oxidation with hydrogen peroxide.

The process according to the invention, using dimethyl sulphoxide, leads to a yield of 25 percent, while a yield of only 10 percent is obtained with hydrogen peroxide.

EXAMPLE 29

The process which is described in Examples 1 to 26 is applied to the treatment of dibenzyl sulphide with dimethyl sulphoxide. There is then obtained dibenzyl sulphoxide (C$_6$H$_5$CH$_2$)$_2$SO, with a yield of 25 percent, while this yield does not exceed 10 percent when the dibenzyl sulphide is treated with other oxidants.

I claim:

1. In a process for producing an organic sulphoxide by reacting the corresponding sulphide with an organic sulphoxide having a lower molecular weight than the desired sulphoxide in the presence of a catalyst at elevated temperature equal to or below the boiling point of the reaction mixture, the improvement which comprises employing 1–3 percent by volume based on the volume of said lower molecular weight sulphoxide of an aqueous acidic solution of a strong electrolyte as the catalyst wherein said aqueous solution contains 0.1–10 mols per liter of a strong acidic electrolyte selected from the group consisting of perchloric acid, hydrochloric acid, hydrofluoric acid, hydriodic acid, nitric acid, and the ammonium salts thereof.

2. The process of claim 1 wherein said catalyst is employed in an amount such that there are about 0.5–3 gram ions of hydrogen per 100 mols of sulphide.

3. The process of claim 1 wherein the amount of lower molecular weight sulphoxide is 1.1–2 mols per mol of said sulphide.

4. The process of claim 1 wherein an inert gas is blown through the reaction medium to produce the entrainment of the sulphide formed by the reaction.

5. The process of claim 1 wherein said strong electrolyte is HC1O$_4$.

6. The process of claim 1 wherein said strong electrolyte is HCl or HNO$_3$.

7. The process of claim 1 wherein said strong electrolyte is NH$_4$I.

8. The process of claim 5 wherein said strong electrolyte additionally contains NH$_4$Br.

9. The process of claim 1 wherein the organic moieties of said sulphide are individually selected from the group consisting of alkyl, hydroxyalkyl, cycloalkyl, aryl, or said substituents are linked to form a tetramethylene group; said lower molecular weight sulphoxide is dimethyl sulfoxide and is used in an amount of 1.1–2 mols per mol of said sulphide, the elevated temperature is 150°–250° C., said aqueous solution contains 0.1–10 mols of said strong electrolyte per liter, and said aqueous solution is used in an amount sufficient to provide about 0.5–3 gram ions of hydrogen ions per 100 mols of said sulphide.

* * * * *